United States Patent [19]

Brennan

[11] Patent Number: 5,094,594
[45] Date of Patent: Mar. 10, 1992

[54] PIEZOELECTRIC PUMPING DEVICE

[75] Inventor: Thomas M. Brennan, Hillsboro, Calif.

[73] Assignee: Genomyx, Incorporated, South San Francisco, Calif.

[21] Appl. No.: 512,957

[22] Filed: Apr. 23, 1990

[51] Int. Cl.$^5$ ............... F04B 17/00; A61N 1/30; A61F 13/00
[52] U.S. Cl. ................... 417/322; 417/415; 604/20
[58] Field of Search ............ 417/322, 415; 604/20; 128/198

[56] References Cited

U.S. PATENT DOCUMENTS

| | | | |
|---|---|---|---|
| 4,450,375 | 5/1984 | Siegal | 310/331 |
| 4,498,851 | 2/1985 | Kolm et al. | 417/322 |
| 4,629,926 | 12/1986 | Siegal | 310/331 |
| 4,638,338 | 1/1987 | Elrod | 346/140 |
| 4,708,600 | 11/1987 | AbuJudom | 417/322 |
| 4,733,121 | 3/1988 | Hebert | 310/311 |
| 4,758,226 | 7/1988 | Carre | 604/141 |
| 4,938,742 | 7/1990 | Smits | 417/322 |
| 5,019,034 | 5/1991 | Weaver et al. | 604/20 |

OTHER PUBLICATIONS

Kyser et al., "Design of an Impulse Ink Jet", Journal of Applied Photographic Engineering, vol. 7, No. 3, Jun. 1981.

Primary Examiner—Richard A. Bertsch
Assistant Examiner—Alfred Basichas
Attorney, Agent, or Firm—Allegretti & Witcoff, Ltd.

[57] ABSTRACT

The invention herein provides a picoliter fluid pumping device in combination with an electrophoresis unit. The picoliter fluid pumping device includes an actuating unit, for selectively generating pump actuating signals, and a pump unit. The pump unit includes a deforming means, a deformable fluid chamber having a deformable chamber segment, a nozzle port, and an inlet port coupled to a fluid source to provide a fluid to the deformable fluid chamber. The deforming means, coupled to the actuating unit, deforms the deformable chamber segment in response to a pump actuating signal to cause a picoliter quantity of the fluid to be emitted from the nozzle port. The picoliter fluid pumping device has in combination an electrophoresis unit having at least one electrophoresis electrode coupled to the deformable fluid chamber and spatially located near the nozzle port and at least one electrophoresis port coupled to the deformable fluid chamber and spatially located near the nozzle port.

15 Claims, 3 Drawing Sheets

PIEZO ELECTRIC

SECTION VIEW

PIEZOELECTRIC PUMPING DEVICE

BACKGROUND OF THE INVENTION

This invention relates to fluid pumping devices and more particularly to fluid pumping devices that emit small quantities of fluid having a volume in the order of picoliters.

Fluid pumping devices have a wide variety of applications and are designed according to the specific application. In medical diagnostic applications, for example, fluid pumping devices are incorporated into diagnostic systems that require these devices to supply small, accurate, quantities of fluid. Medical diagnostic applications include, for example, combustion and mass spectrometric analysis systems, microfraction collector devices, and digital ultramico pipette devices.

In combustion and mass spectrometric analysis systems, for example, a fluid pumping device continually sweeps an electrophoresis column and ejects the effluent into a pyrolyzer oven. The accuracy of the analysis is dependent, on the pumping device providing accurate, highly repeatable, small quantities of fluid. That is to say, as the volume of the fluid decreases, the concentration of ions injected into the pyrolyzer oven increases, and accordingly facilitates an increase in accuracy of the analysis. As is known by those skilled in the art, systems employing electrophoresis techniques are valuable diagnostic tools in the quantitative study of individual molecules in a complex natural mixture such as blood and other body fluids DNA, RNA, and polypeptides are often separated by electrophoresis.

Conventional fluid pumping devices lack the ability of providing highly accurate, highly repeatable small quantities of fluid; fluid quantities having a volume in the order of picoliters. Conventional fluid pumping device designs do not lend themselves to supply accurate highly repeatable small quantities of fluid required in highly accurate analyzing systems. Consequently, there exists a need for fluid pumping devices that can selectively eject a fluid having a volume in the order of picoliters.

DESCRIPTION OF THE PRIOR ART

The U.S. Pat. No. 4,450,375 Siegal, U.S. Pat. No. 4,498,851 - Kolm et al., U.S. Pat. No. 4,629,926 -Siegal, U.S. Pat. No. 4,638,338 - Elrod, U.S. Pat. No. 4,708,600 - AbuJudom, II et al., U.S. Pat. No. 4,733,121 - Hebert, and U.S. Pat. No. 4,758,226 - Carre are believed to be typical examples of some conventional fluid pumping devices.

The Siegal patents U.S. Pat. Nos. 4,450,375 and 4,629,926 are believed to be directed to piezoelectric spring bender mechanisms. These mechanisms control flow past a valve seat responsive to an electric signal or condition, and include rapid and accurate control of the fluids under pressures in a variety of different applications such as fluidics.

Elrod U.S Pat. No. 4,638,338 shows a capillary wave controller for multiple ejector arrays, including providing nozzleless droplet ejectors of various types.

AbuJudom, II et al. U.S. Pat. No. 4,708,600 is believed to disclose a piezoelectric pumping arrangement for supplying fluid under pressure, including first and second PE laminates; use is shown to include powering one or more fluid pumps, HVAC pneumatic control systems, and capable of being readily integrated into a structure of a pneumatic cylinder.

Carre U.S. Pat. No. 4,758,226 is believed to be directed to dispensing, for medical applications, of a product from a tank in determined metered amounts and having two adjacent valves, a calibrated nozzle, and electronic means provided to control deformation of piezoelectric crystals to control the output of the product from the tank.

SUMMARY OF THE INVENTION

Accordingly, the invention herein provides a picoliter fluid pumping device comprising an actuating unit, for selectively generating pump actuating signals, and a pump unit. The pump unit includes a deforming means, a deformable fluid chamber having a deformable chamber segment, a nozzle port, and an inlet port coupled to a fluid source to provide a fluid to the deformable fluid chamber. The deforming means, coupled to the actuating unit, deforms the deformable chamber segment in response to a pump actuating signal to cause a small quantity of the fluid to be emitted from the nozzle port.

The pump unit may include a nozzle capillary for coupling the nozzle port to the fluid cavity and an inlet capillary for coupling the inlet port to the fluid cavity. In addition, the pump unit may include an inlet flutter valve for inhibiting the fluid from entering the deformable chamber in response to an inlet flutter actuating signal. The pump unit may further include a nozzle flutter valve a nozzle flutter valve, spatially positioned in the nozzle capillary for inhibiting the fluid from exiting the deformable chamber in response to a nozzle flutter actuating signal. The actuating unit sequentially and selectively provides the nozzle and inlet flutter actuating signals to the nozzle and inlet flutter valves.

In one embodiment, the deforming means is a piezoelectric crystal having a substantially planar surface mechanically coupled to the deformable chamber segment of the fluid chamber. Furthermore, the nozzle and inlet flutter valves may be piezoelectric crystals having a substantially planar surface also mechanically coupled to the deformable chamber segment of the fluid chamber.

In another embodiment the picoliter fluid pumping device includes an electrophoresis unit having at least one electrophoresis electrode coupled to the deformable fluid chamber and spatially located near the nozzle port, and at least one electrophoresis port coupled to the deformable fluid chamber and spatially located near the nozzle port. The electrophoresis port is coupled to a second fluid source to provide a second fluid to the deformable fluid chamber. In addition, the electrophoresis unit further includes an electrophoresis electrical potential generating unit coupled to the second fluid source and the electrophoresis electrode for providing an electrical potential there between.

The electrophoresis electrode may be spatially located in the nozzle capillary. In addition, the electrophoresis port may also be also spatially located in the nozzle capillary substantially opposite the electrophoresis electrode.

DETAILED DESCRIPTION

Briefly, the picoliter fluid pumping device is a highly accurate, highly repeatable fluid pump that is capable of providing small quantities of fluid having a volume in the order of picoliters. The picoliter fluid pumping device includes a pump unit and an actuator unit. The actuator unit provides a user definable actuating signal to actuate the pump unit. In response, the pump unit emits a small quantity of fluid in the order of picoliters.

The pumping device may further include an electrophoresis unit coupled to the pump unit thereby allowing the pumping device to be implemented in analyzing systems utilizing electrophoresis techniques. The electrophoresis unit establishes a voltage gradient within a second fluid containing electrically charged ions suspended in that fluid. Upon actuating the pump unit, a small quantity of both fluids are emitted from the pump unit.

Figure 1:
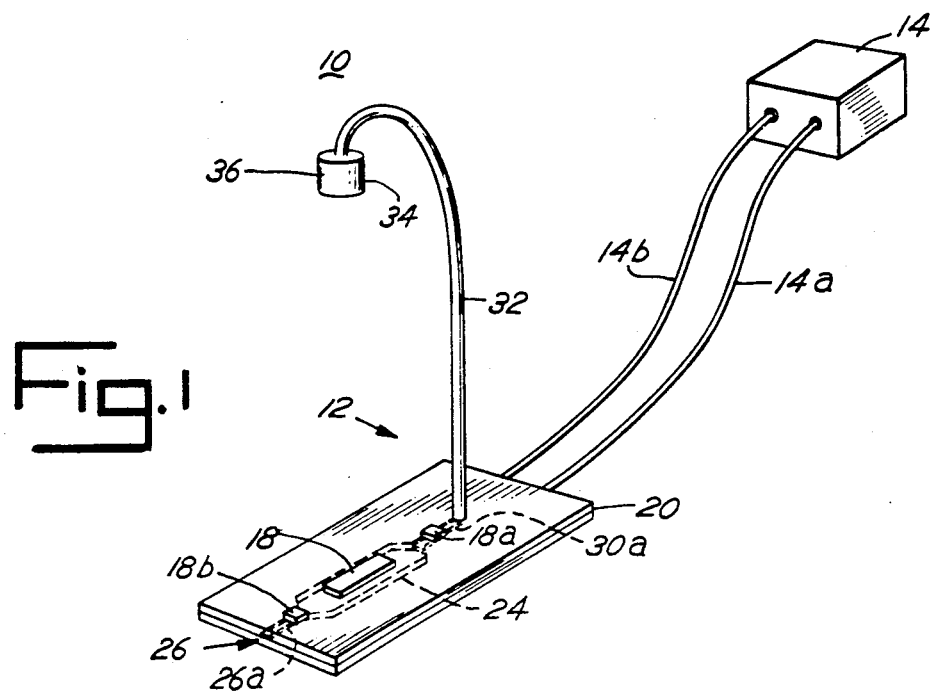
FIG. 1 is a schematic diagram of a picoliter fluid pumping device in accordance with the present invention.

FIG. 1 illustrates, in a schematic diagram, an embodiment of picoliter fluid pumping device 10 of the present invention. Picoliter fluid pumping device 10 includes a pump unit 12, an actuator unit 14, for example a pulse generator, and an electrophoresis unit 16.

Figure 2:
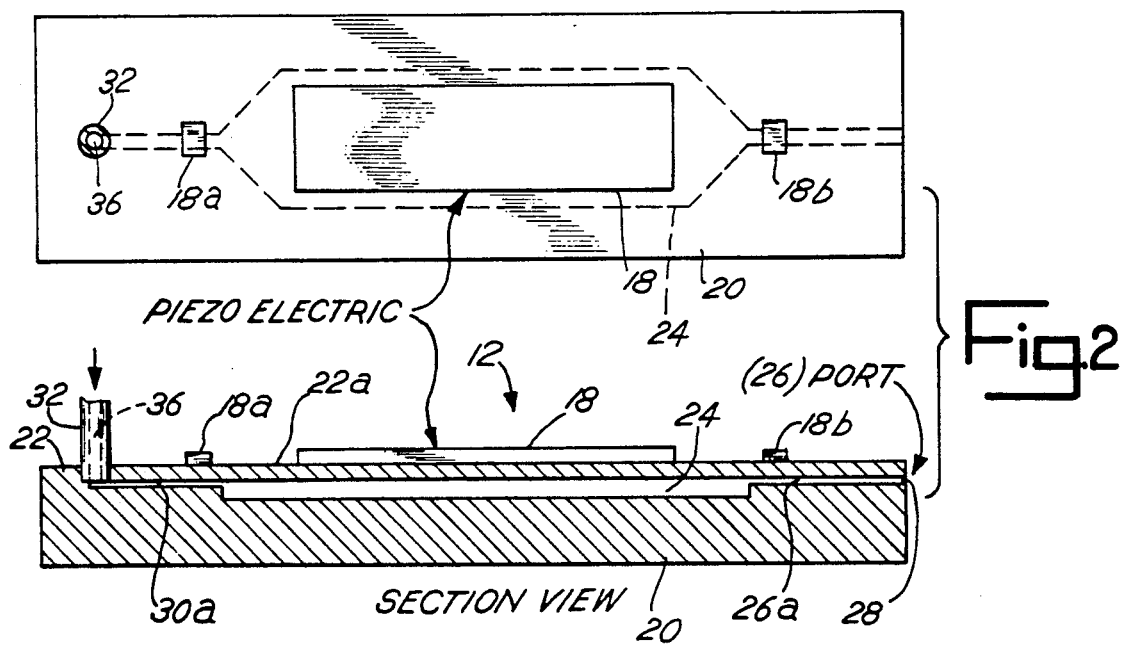
FIG. 2 is a perspective view of the pump unit of the picoliter fluid pumping device shown in FIG. 1.

Referring to FIGS. 1 and 2, pump unit 12 includes a piezo-pump element 18, for example a piezoelectric crystal, a pump chamber base 20, a pump chamber cover 22 having a deformable chamber segment 22a, a pump cavity 24, a nozzle port 26 having an orifice 28, and an inlet port 30. Pump unit 12 further includes a nozzle capillary 26a which connects pump cavity 24 to nozzle port 26, and an inlet capillary 30a which connects pump cavity 24 to inlet port 30. In addition, pump unit 12 includes a sweep fluid tube 32 coupled to a sweep fluid housing 34 containing a sweep fluid 36.

Piezo-pump element 18 is mechanically coupled to at least a portion of deformable chamber segment 22a of pump chamber 20. In addition, piezo-pump element 18 is electrically coupled to actuator unit 14 via lines 14a and 14b.

In operation, picoliter fluid pumping device 10 utilizes actuator unit 14 to initiate the pumping of sweep fluid 36. Actuator unit 10 applies a pump actuation signal on lines 14a and 14b which causes piezo-pump element 18 to expand. The actuation and corresponding expansion of piezo-pump element 18 causes deformable chamber segment 22a to deform and thereby compress pump cavity 24. The compression of pump cavity 24 forces sweep fluid 36 to exit pump cavity 24 and flow toward nozzle port 26 and inlet port 30. Consequently, sweep fluid 36 is forced to flow through nozzle capillary 26a and exist pump unit 12 at nozzle port 26. When the restrictions to flow of fluid 36 are about equal at both the inlet and nozzle paths, about half of sweep fluid 36 forced out of pump cavity 24 traverses the nozzle path.

The pumping or compression effect within pump cavity 24, produced by the deformation of piezo-pump element 18, must provide sweep fluid 36 with sufficient momentum to overcome the surface tension at nozzle port 26. The compression of pump cavity 24 must supply sufficient energy to fluid 36 such that a small quantity of sweep fluid 36 at nozzle port 26 "breaks off" as deformable chamber segment 22a attains maximum deflection.

After piezo-pump element 18 attains maximum deflection, actuator unit 14 removes the pump actuation signal thereby de-actuating piezo-pump element 18. In response, pump cavity 24 "springs back" to its pre-actuated state thus drawing sweep fluid 36 from the inlet and nozzle paths into pump cavity 24. Inlet capillary 30a will be substantially filled when pump cavity 24 springs back to its pre-actuated state due to its connection to sweep fluid housing 34. Nozzle capillary 26a, however, will be initially only partially filled since a small quantity of sweep fluid 26 was emitted during the pumping action. Nozzle capillary 26a attains a substantially filled state through capillary action (when fluid 36 is a liquid the force of a hydrophylic liquid wetting a glass surface) once pump cavity 24 returns to a steady state condition. After nozzle capillary has refilled, the fluid emitting sequence/cycle may be repeated.

The fluid ejection rate is user selectable. That is to say the user may select the rate of actuation of piezo-pump element 18. The user controls the fluid ejection rate by selecting the rate at which actuator unit 14 applies pump actuating signals to piezo-pump element 18. The fluid ejection sequence rate is primarily limited by the refill rate of the nozzle path. Proper operation of device 10 requires that nozzle capillary 26 and nozzle port 26a be substantially filled with sweep fluid 36 prior to applying a pump actuation signal.

Pump unit 12 may also include an inlet and nozzle piezo-flutter check valves 18a and 18b, respectively, to permit picoliter fluid pumping device 10 to operate against pressure gradients in either direction. That is to say, when picoliter fluid pumping device 10 is operating in an environment having a pressure not equal to pressure of sweep fluid 26, appropriate actuation of inlet and nozzle piezo-flutter valves 18a and 18b permits device 10 to function effectively. The piezo-flutter valves are coupled to actuator unit 14 and are spatially positioned on each side of pump cavity 24 as illustrated in FIG. 2. Piezo-flutter valves 18a and 18b may be, for example, piezoelectric crystals having similar characteristics as the piezoelectric crystal of piezo-pump 18. Furthermore, piezo-flutter valves 18a and 18b may be actuated in a substantially similar manner as piezo-pump element 18.

When picoliter fluid pumping device 10 is operating in an ambient environment having a pressure that is greater than that of sweep fluid 36, actuator unit 14 applies an inlet actuation signal to inlet piezo-flutter valve 18a. In response, inlet piezo-flutter valve 18a expands and causes local deformation of deformable chamber segment 22a at inlet capillary 30a and substantially restricting sweep fluid 26 from entering pump cavity 24 from inlet port 30. The nozzle piezo-flutter valve 186 is not actuated. In this piezo-flutter valve state, actuator unit 14 applies a pump actuation signal to piezo-pump element 18 thereby deforming deformable chamber segment 22a and establishing the compression effect in pump cavity 24 as described above.

At maximum deflation of piezo-pump element 18 and after a small quantity of sweep fluid 36 has been emitted as described above, actuator unit 14 applies a nozzle actuation signal to nozzle piezo-flutter valve 18b. Deformable chamber segment 22a is locally deformed at nozzle capillary 26a thereby substantially restricting sweep fluid 26 from entering nozzle capillary 26a or eniting pump cavity 24. Actuator unit 14 then removes the pump actuation signal from piezo-pump element 18 and the inlet actuation signal from inlet piezo-flutter valve 18a in succession.

Actuator unit 14 de-activates inlet piezo-flutter valve 18a to allow sweep fluid 26 to enter pump cavity 24 from inlet port 30 until pump cavity is refilled. Actuator unit 14 then activates inlet piezo-flutter valve 18a and de-activates nozzle piezo-flutter valve 18b in succession and the pumping cycle continues as described above. As before, the pumping rate is user selectable.

Figure 3:
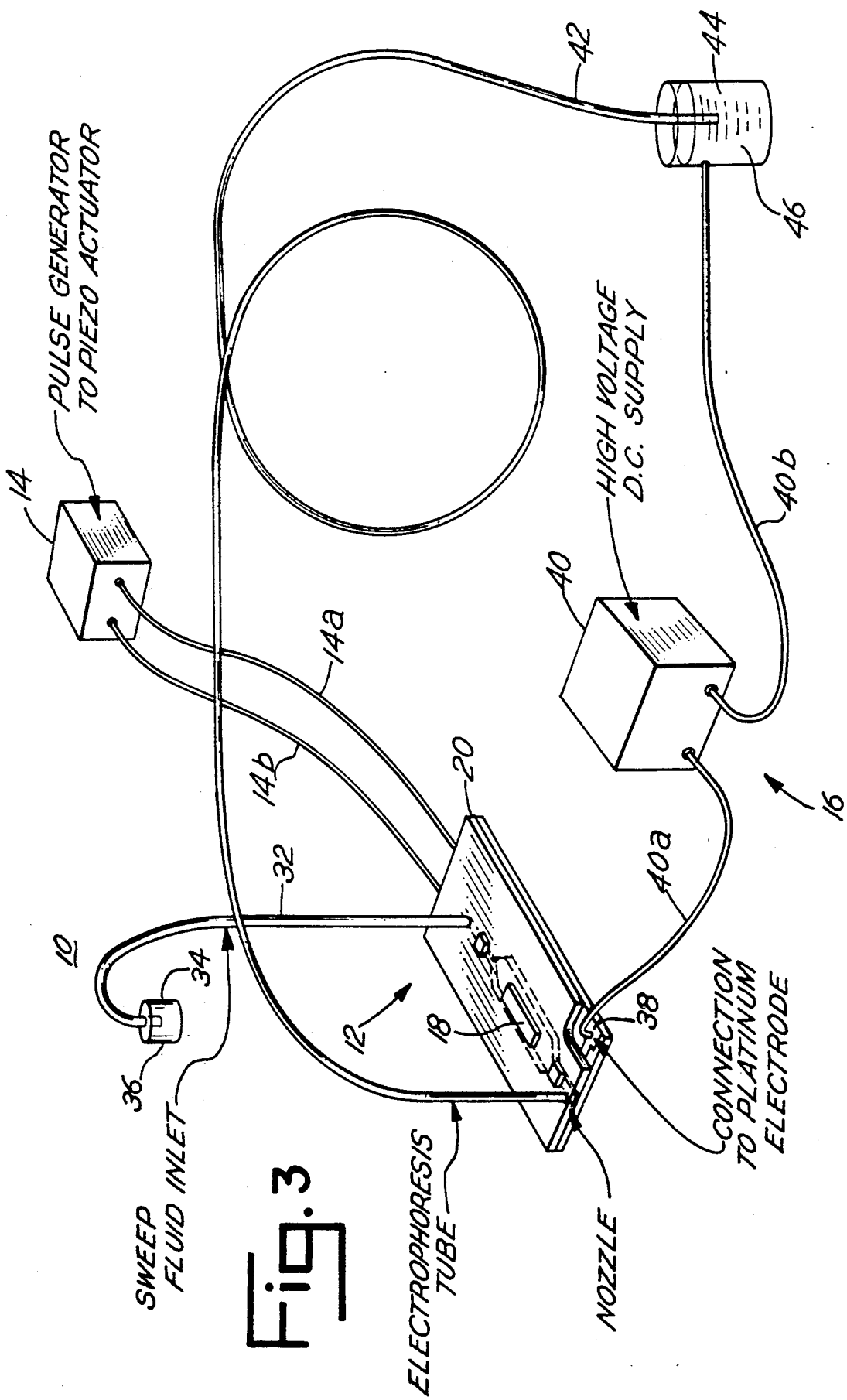
FIG. 3 is a schematic diagram of a picoliter fluid pumping device including an electrophoresis unit.

FIG. 3 illustrates, in a schematic diagram, a picoliter fluid pumping device including an electrophoresis unit 16. In the illustrative embodiment, electrophoresis unit 16 includes an electrophoresis electrode 38, an electrical potential generating unit 40, for example a high voltage dc power supply, an electrophoresis fluid tube 42 coupled to an electrophoresis fluid 15 housing 44 containing an electrophoresis fluid 46. Electrophoresis unit 16 further includes an electrophoresis port 41 spatially positioned between nozzle port 26 and pump cavity 24.

Electrical potential generating unit 40 is electrically coupled to electrophoresis electrode 38 via line 40a. In addition, electrical potential generating unit 40 is electrically coupled to electrophoresis fluid housing 44, via line 40b, thereby establishing and maintaining an electrical potential between electrode 38 and fluid housing 44.

In operation, particles that are attracted to electrophoresis electrode 38 enter nozzle capillary 26a through electrophoresis port 41. These charged particles collect near the center of nozzle capillary 26a and are emitted during the pumping sequence. Note, pump unit 12 operates in an identical manner to that as described above.

Figure 4:
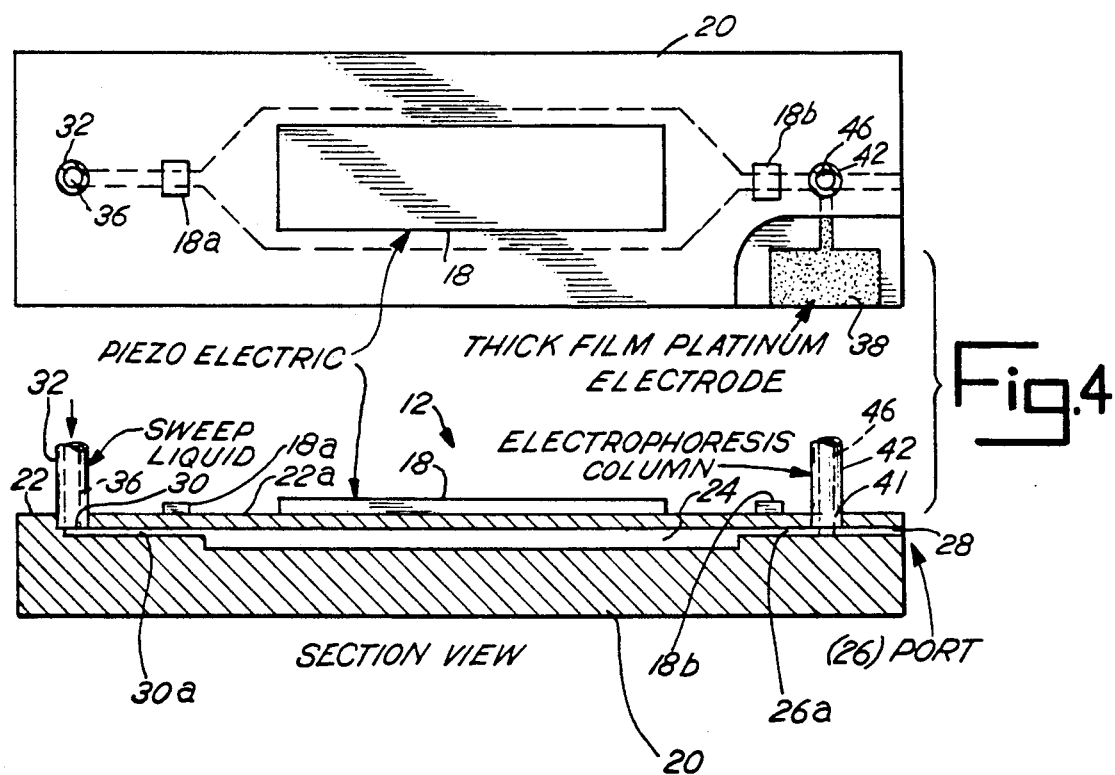
FIG. 4 is a perspective view of the pump unit of the picoliter fluid pumping device shown in FIG. 3 including several electrophoresis elements.

FIG. 4 illustrates a preferred embodiment of the relative spatially positions of electrophoresis port 41 and electrophoresis electrode 38 of electrophoresis unit 14, and nozzle port 26 and nozzle capillary 26a of pump unit 12. Electrophoresis port 41 and electrophoresis electrode 38 are spatially positioned in nozzle capillary 26a "down stream" from nozzle port 26. Furthermore, electrophoresis port 41 and electrophoresis electrode 38 are configured substantially opposite each other. Consequently, the charged particles in electrophoresis fluid 46 enter pump unit 12 near nozzle port 26 through electrophoresis port 41 and are attracted to electrode 38. The charged particles, however, encounter sweep fluid 36 which impedes their motion and the charged particles collect near the center of nozzle capillary 26a. An advantage of this configuration is that a substantial quantity of charged particles within electrophoresis fluid 46 will collect near the center of nozzle capillary 26a and will be emitted during the pumping action of pump unit 12.

In an illustrative embodiment, pump cavity 24 has nominal dimensions of 0.6 inch length ×0.1 inch width ×350 micron depth. Inlet capillary 30a and nozzle capillary 26a have dimensions of 350 micron length ×70 micron width ×70 micron depth. Nozzle port 26 may have substantially similar cross sectional dimensions as nozzle capillary 26a.

Pump chamber base 20 may be fabricated from, for example, glass of the type PhotoCeram, from Corning Glass, Ithica, N.Y.. Pump cavity 22 may be etched into pump chamber base 20 utilizing photolitography. Nozzle and inlet ports 26 and 30, as well as the nozzle and inlet capillaries 26a and 30a, may also be etched into the pump base using photolitography.

Piezo-pump element 18 may be a piezoelectric crystal, manufactured by Piezokinetics, Inc., Bellefonte, PA 16823. A picoliter pump device having the above characteristics may be actuated using an actuating signal of approximately 80 volts. At maximum deflection there exists sufficient deformation of pump cavity 24 to cause sweep fluid 26 to overcome the surface tension at nozzle port 26 and emit a small quantity of fluid.

The diameter and quantity of sweep fluid 26 emitted, for a single pump actuation signal, is substantially dependent upon the dimensions of nozzle port 26 and nozzle orifice 26a. As an illustration, a 70 micron square channel will produce fluid ejection having diameter of approximately 100 micron and a volume of approximately 500 picoliters. Furthermore, a 35 micron channel will produce fluid ejection having diameter of approximately 50 micron and a volume of approximately 65 picoliters.

Preferred embodiments of the present invention have been described herein. It is to be understood that modifications and changes can be made without departing from the true scope and spirit of the present invention, which are defined by the following claims to be interpreted in view of the foregoing description.

What is claimed is:

1. A picoliter fluid pumping device comprising:
   actuating means for selectively providing pump actuating signals;
   a pump unit, coupled to said actuating means, including:
      a fluid chamber having a deformable chamber segment, a nozzle port, and an inlet port coupled to a first fluid source to provide a first fluid to said fluid chamber;
   electrophoresis unit including:
      at least one electrophoresis electrode coupled to said deformable fluid chamber and spatially located near said nozzle port;
      at least one electrophoresis port coupled to said deformable fluid chamber and spatially located near said nozzle port and coupled to a second fluid source to provide a second fluid to said fluid chamber;
   electrophoresis potential means coupled to said second fluid source and said electrophoresis electrode for providing an electrical potential there between; and
   wherein said pump unit further includes deforming means, coupled to said actuating means and said deformable fluid chamber, for deforming said fluid chamber in response to said pump actuating signal and thereby causing a small quantity of said first and second fluid, to be emitted from said nozzle port.

2. The pumping device of claim 1 wherein said deforming means includes a piezoelectric crystal, responsive to said pump actuating signals and having a substantially planar surface mechanically coupled to at least a portion of said deformable chamber segment of said fluid chamber.

3. The pumping device of claim 1 or 2 wherein said pump unit further includes:
   a nozzle capillary to couple said nozzle port to said fluid chamber; and
   an inlet capillary to couple said inlet port to said fluid chamber.

4. The picoliter fluid pumping device of claim 3 wherein said nozzle capillary has first surface and said electrophoresis electrode is spatially located in said first surface.

5. The picoliter fluid pumping device of claim 4 wherein said nozzle capillary has a second surface substantially opposite said first surface and said electrophoresis port is spatially located in said second surface.

6. The picoliter fluid pumping device of claim 5 wherein said electrophoresis electrode is spatially located substantially opposite said electrophoresis port.

7. The pumping device of claim 1 wherein said nozzle port includes an orifice having a surface area of less than 4400 microns$^2$.

8. The pumping device of claim 1 wherein said nozzle port includes an orifice having a surface area of about than 1225 microns$^2$.

9. The pumping device of claim 1 wherein said first and second fluid emitted has a volume of about 65 picoliters per pump actuating signal.

10. The pumping device of claim 1 wherein said first and second fluid emitted has a volume of less than 500 picoliters per pump actuating signal.

11. The pumping device of claim 1 wherein said actuating means provides an actuating signal at a rate greater than about 10 cycles/sec.

12. The pumping device of claim 1 wherein said actuating means provides an actuating signal at a rate greater than about 1000 cycles/sec.

13. The pumping device of claim 1 wherein said actuating means provides an actuating signal at a rate of about 3000 cycles/sec.

14. The pumping device of claim 1 wherein said actuating means further provides flutter actuating signals and wherein said device further includes:
a nozzle flutter valve means, electrically coupled to said actuating means and mechanically coupled to said deformable fluid chamber near said first port, for inhibiting said first and second fluids from leaving said chamber in response to said flutter actuating signal; and
an inlet flutter valve means, electrically coupled to said actuating means and mechanically coupled to said deformable fluid chamber near said second port, for inhibiting said first fluid from entering said chamber in response to said flutter actuating signal.

15. The pumping device of claim 14, operating in an ambient environment having an ambient pressure, wherein said first and second fluid in said chamber have a pressure not equal to said ambient pressure.

* * * * *